US012784219B2

(12) United States Patent
Li et al.

(10) Patent No.: US 12,784,219 B2
(45) Date of Patent: Nov. 3, 2026

(54) FFR DETERMINATION METHOD AND APPARATUS BASED ON MULTI-MODAL MEDICAL IMAGE, DEVICE, AND MEDIUM

(71) Applicant: Suzhou Pulse Rongying Medical Technology Co., Ltd, Suzhou (CN)

(72) Inventors: Yingguang Li, Suzhou (CN); Li Ling, Suzhou (CN); Xun Liu, Suzhou (CN)

(73) Assignee: Suzhou Pulse Rongying Medical Technology Co., Ltd., Jiangsu (CN)

( * ) Notice: Subject to any disclaimer, the term of this patent is extended or adjusted under 35 U.S.C. 154(b) by 330 days.

(21) Appl. No.: 18/691,793

(22) PCT Filed: Aug. 17, 2022

(86) PCT No.: PCT/CN2022/113089
§ 371 (c)(1),
(2) Date: Mar. 13, 2024

(87) PCT Pub. No.: WO2023/040560
PCT Pub. Date: Mar. 23, 2023

(65) Prior Publication Data
US 2024/0320831 A1 Sep. 26, 2024

(30) Foreign Application Priority Data
Sep. 14, 2021 (CN) ......................... 202111073928.9

(51) Int. Cl.
*G06T 7/00* (2017.01)
*A61B 6/00* (2006.01)
(Continued)

(52) U.S. Cl.
CPC ............ *G06T 7/0014* (2013.01); *A61B 6/507* (2013.01); *A61B 6/5247* (2013.01); *G06T 7/337* (2017.01);
(Continued)

(58) Field of Classification Search
CPC .................. G06T 7/0014; G06T 7/337; G06T 2207/20221; G06T 2207/30104;
(Continued)

(56) References Cited

U.S. PATENT DOCUMENTS

2013/0072805 A1* 3/2013 Schmitt ................ G06T 7/0012 600/479
2013/0226003 A1* 8/2013 Edic ....................... A61B 6/507 600/504
2019/0110776 A1* 4/2019 Yu ....................... A61B 5/0035

FOREIGN PATENT DOCUMENTS

CN 107730540 A 2/2018
CN 209269681 U 8/2019
(Continued)

OTHER PUBLICATIONS

International Search Report; China National Intellectual Property Administration; International Application No. PCT/CN2022/113089; Nov. 18, 2022; 8 pages.

*Primary Examiner* — Gregory A Morse
*Assistant Examiner* — Renae A Bitor
(74) *Attorney, Agent, or Firm* — Taft Stettinius & Hollister LLP

(57) ABSTRACT

The present invention provides an FFR determination method and apparatus based on multi-modal medical image, a device, and a medium. The method includes: obtaining an intravascular image comprising a blood vessel segment of interest; obtaining an extravascular image comprising a blood vessel segment to be detected, where the blood vessel segment to be detected at least partially coincides with the blood vessel segment of interest; performing registration on the intravascular image and the extravascular image to obtain a registration result; and determining a target fractional flow reserve based on multi-modal medical image by using the registration result on the basis of the intravascular
(Continued)

image and the extravascular image. In the FFR determination method of the present invention, calculation of the fractional flow reserve is optimized by utilizing the registration result of the intravascular image and the extravascular image and integrating advantageous information of the intravascular image and the extravascular image, so as to obtain the fractional flow reserve which is based on multimodal medical image and has both blood vessel segment integrity and local accuracy, thereby improving the accuracy and stability of fractional flow reserve calculation.

12 Claims, 6 Drawing Sheets

(51) Int. Cl.
*A61B 6/50* (2024.01)
*G06T 7/33* (2017.01)

(52) U.S. Cl.
CPC ............... *G06T 2207/20221* (2013.01); *G06T 2207/30104* (2013.01)

(58) Field of Classification Search
CPC . G06T 2207/10101; G06T 2207/30101; G06T 7/0012; G06T 7/0016; A61B 6/507; A61B 6/5247; A61B 5/0035; A61B 5/0261; A61B 5/0263; A61B 6/032; A61B 6/469; A61B 6/481; A61B 6/487; A61B 6/504; A61B 6/5217; A61B 6/5235; A61B 5/0066; A61B 5/029; A61B 5/748
See application file for complete search history.

(56) References Cited

FOREIGN PATENT DOCUMENTS

| | | | | | |
|---|---|---|---|---|---|
| CN | 111134651 A | * | 5/2020 | ......... | A61B 5/02007 |
| CN | 111523538 A | | 8/2020 | | |
| CN | 112509020 A | | 3/2021 | | |
| CN | 113180631 A | | 7/2021 | | |
| CN | 113616160 A | | 11/2021 | | |

* cited by examiner

FFR DETERMINATION METHOD AND APPARATUS BASED ON MULTI-MODAL MEDICAL IMAGE, DEVICE, AND MEDIUM

CROSS-REFERENCE TO RELATED APPLICATIONS

This application is a U.S. National Phase of International PCT Application No. PCT/CN2022/113089 filed on Aug. 17, 2022, which claims priority to Chinese Patent Application Serial No. 202111073928.9 filed on Sep. 14, 2021. The contents of those applications are incorporated herein by reference in their entireties.

TECHNICAL FIELD

The present invention relates to the field of intravascular interventional imaging medical devices, and in particular, to an FFR determination method and apparatus based on multi-modal medical image, a device, and a medium.

BACKGROUND

Coronary artery disease has become the number one cause of death worldwide. Currently, percutaneous coronary intervention (Percutaneous Coronary Intervention, PCI) treatment is one of the effective treatments for coronary artery disease.

A fractional flow reserve (Fractional flow reserve, FFR) is assessed by measuring a pressure difference between the distal and proximal ends of the coronary artery stenosis, and can effectively reflect the impact of the stenotic lesion on the blood supply function of the blood vessel and evaluate whether the stenotic lesion causes ischemia of the coronary myocardium perfusion. At present, the FFR has become the gold standard for clinical diagnosis, guidance and evaluation of PCI treatment.

However, for the traditional FFR, a blood pressure needs to be measured through a pressure guide wire. This inspection operation is complex and time-consuming, and the required surgical consumables (FFR guide wire) are expensive. In addition, the side effects of injecting vasodilator drugs can cause discomfort to the patient, and the guide wire can easily cause damage to the blood vessels of the patient during the intervention process. The above reasons limit the promotion of the pressure guide wire method for measuring the FFR.

In addition, existing methods for calculating the FFR through imaging are usually based on vascular imaging technologies, such as X-ray angiography imaging, computed tomography (Computed Tomography, CT) imaging, and optical coherence tomography (Optical Coherence Tomography, OCT) imaging, and Intravenous Ultrasound (Intravenous Ultrasound, IVUS) imaging technology, to obtain extravascular images or intravascular images, and then obtain blood vessel lumen information, and calculate the fractional flow reserve by using methods such as fluid dynamics analysis, biomechanical analysis, and vascular histological analysis.

However, due to the limited imaging length when collecting the intravascular images, sometimes the entire diseased blood vessel cannot be completely covered. Therefore, the blood vessel segment expressed by the fractional flow reserve calculated based on the intravascular images is incomplete. In addition, because the range of observation for a branch vessel in the intravascular image is quite short, the shunting of blood flow by the branch vessel cannot be accurately determined. At the same time, the intravascular image cannot reflect the overall spatial information of the blood vessel, especially the curvature information, and consequently calculation errors are easily introduced. Compared with the intravascular image, the extravascular image can better display the overall spatial information of the blood vessel segment to be detected. The blood vessel segment expressed by the fractional flow reserve calculated based on the extravascular image is more complete, but local accuracy is often weaker than the intravascular image.

SUMMARY

In view of the above problems of the prior art, an objective of the present invention is to provide an FFR determination method and apparatus based on multi-modal medical image, a device, and a medium, to improve accuracy and stability of calculation of the fractional flow reserve.

To solve the problems, the present invention provides an FFR determination method based on multi-modal medical image, including:

- obtaining an intravascular image comprising a blood vessel segment of interest;
- obtaining an extravascular image comprising a blood vessel segment to be detected, where the blood vessel segment to be detected at least partially coincides with the blood vessel segment of interest;
- performing registration on the intravascular image and the extravascular image to obtain a registration result; and
- determining a target fractional flow reserve based on multi-modal medical image by using the registration result on the basis of the intravascular image and the extravascular image.

Further, the performing registration on the intravascular image and the extravascular image to obtain a registration result includes:

- obtaining a first feature information of the blood vessel segment of interest in the intravascular image, where the first feature information includes internal lumen information of the blood vessel segment of interest;
- obtaining a second feature information of the blood vessel segment to be detected in the extravascular image, where the second feature information includes external lumen information of the blood vessel segment to be detected; and
- performing registration based on the first feature information and the second feature information to obtain a registration result.

Further, the determining a target fractional flow reserve based on multi-modal medical image by using the registration result on the basis of the intravascular image and the extravascular image includes:

- determining a first retracement curve corresponding to a fractional flow reserve of the blood vessel segment of interest based on the intravascular image;
- determining a second retracement curve corresponding to a fractional flow reserve of the blood vessel segment to be detected based on the extravascular image; and
- determining a target fractional flow reserve based on multi-modal medical image by using the registration result on the basis of the first retracement curve and the second retracement curve.

Optionally, the determining a first retracement curve corresponding to a fractional flow reserve of the blood vessel segment of interest based on the intravascular image includes:

obtaining a blood flow velocity of the blood vessel segment to be detected; and determining a first retracement curve corresponding to a fractional flow reserve of the blood vessel segment of interest based on the intravascular image and the blood flow velocity.

Optionally, the determining a first retracement curve corresponding to a fractional flow reserve of the blood vessel segment of interest based on the intravascular image includes:

obtaining a first branch blood vessel information of the blood vessel segment of interest, where the first branch blood vessel information includes branch opening information obtained based on the intravascular image, and branch information obtained based on the extravascular image; and determining a first retracement curve corresponding to a fractional flow reserve of the blood vessel segment of interest based on the intravascular image and the first branch blood vessel information.

Optionally, the determining a second retracement curve corresponding to a fractional flow reserve of the blood vessel segment to be detected based on the extravascular image includes:

obtaining a blood flow velocity of the blood vessel segment to be detected; and determining a second retracement curve corresponding to a fractional flow reserve of the blood vessel segment to be detected based on the extravascular image and the blood flow velocity.

Optionally, the determining a second retracement curve corresponding to a fractional flow reserve of the blood vessel segment to be detected based on the extravascular image includes:

obtaining a second branch blood vessel information of the blood vessel segment to be detected, where the second branch blood vessel information includes branch opening information obtained based on the intravascular image, and branch information obtained based on the extravascular image; and determining a second retracement curve corresponding to a fractional flow reserve of the blood vessel segment to be detected based on the extravascular image and the second branch blood vessel information.

Further, the determining a target fractional flow reserve based on multi-modal medical image by using the registration result on the basis of the first retracement curve and the second retracement curve includes:

determining a first fractional flow reserve sequence based on the first retracement curve, where the first fractional flow reserve sequence is corresponding to a first blood vessel position sequence of the blood vessel segment of interest in the intravascular image;

determining a second fractional flow reserve sequence based on the second retracement curve, where the second fractional flow reserve sequence is corresponding to a second blood vessel position sequence of the blood vessel segment to be detected in the extravascular image, and the second blood vessel position sequence at least partially coincides with the first blood vessel position sequence;

fusing the first fractional flow reserve sequence and the second fractional flow reserve sequence by using the registration result to obtain a target fractional flow reserve sequence; and determining a target fractional flow reserve based on multi-modal medical image on the basis of the target fractional flow reserve sequence.

Further, the fusing the first fractional flow reserve sequence and the second fractional flow reserve sequence by using the registration result to obtain a target fractional flow reserve sequence includes:

calculating a first difference sequence based on the first fractional flow reserve sequence, where a value in the first difference sequence is a decrease value of a fractional flow reserve of a corresponding position relative to a fractional flow reserve of a previous position in the first fractional flow reserve sequence;

calculating a second difference sequence based on the second fractional flow reserve sequence, where a value in the second difference sequence is a decrease value of a fractional flow reserve of a corresponding position relative to a fractional flow reserve of a previous position in the second fractional flow reserve sequence;

fusing the first difference sequence and the second difference sequence by using the registration result to obtain a target difference sequence; and determining the target fractional flow reserve sequence based on the target difference sequence.

Optionally, the determining a target fractional flow reserve based on multi-modal medical image by using the registration result on the basis of the intravascular image and the extravascular image includes:

obtaining a first feature information of the blood vessel segment of interest in the intravascular image, where the first feature information includes internal lumen information of the blood vessel segment of interest;

obtaining a second feature information of the blood vessel segment to be detected in the extravascular image, where the second feature information includes external lumen information of the blood vessel segment to be detected; and calculating the target fractional flow reserve based on multi-modal medical image by using the registration result on the basis of the first feature information and the second feature information.

Optionally, the determining a target fractional flow reserve based on multi-modal medical image by using the registration result on the basis of the intravascular image and the extravascular image includes:

performing image fusion on the intravascular image and the extravascular image by using the registration result to obtain a fused image;

obtaining fusion feature information of the blood vessel segment to be detected in the fused image, where the fusion feature information includes fusion lumen information; and calculating the target fractional flow reserve based on multi-modal medical image on the basis of the fusion feature information.

Another aspect of the present invention provides an FFR determination apparatus based on multi-modal medical image, including:

an intravascular image obtaining module, configured to obtain an intravascular image comprising a blood vessel segment of interest;

an extravascular image obtaining module, configured to obtain an extravascular image comprising a blood vessel segment to be detected, where the blood vessel segment to be detected at least partially coincides with the blood vessel segment of interest;

a registration module, configured to perform registration on the intravascular image and the extravascular image to obtain a registration result; and a fractional flow reserve determining module, configured to determine a target fractional flow reserve based on multi-modal medical image by using the registration result on the basis of the intravascular image and the extravascular image.

Another aspect of the present invention provides an electronic device, including a processor and a memory, at least one instruction or at least one program is stored in the memory, and the at least one instruction or the at least one program is loaded and executed by the processor to implement the FFR determination method based on multi-modal medical image described above.

Another aspect of the present invention provides a computer-readable storage medium, at least one instruction or at least one program is stored in the computer-readable storage medium, and the at least one instruction or the at least one program is loaded and executed by a processor to implement the FFR determination method based on multi-modal medical image described above.

Due to the above technical solution, the present invention has the following beneficial effects:

According to the FFR determination method based on multi-modal medical image according to the embodiments of the present invention, registration is performed on the intravascular image and the extravascular image, and advantageous information of the intravascular image and the extravascular image is integrated by using the registration result, to optimize the calculation of the fractional flow reserve, so that the fractional flow reserve which is based on multi-modal medical image and has both blood vessel segment integrity and local accuracy can be obtained. In this way, accuracy and stability of the calculation of the fractional flow reserve are improved.

BRIEF DESCRIPTION OF DRAWINGS

In order to explain the technical solution of the present invention more clearly, the drawings needed to be used in the embodiments or description of the prior art are briefly introduced below. Obviously, the drawings in the following description are only some embodiments of the present invention. For a person of ordinary skill in the art, other drawings can be obtained based on these drawings without creative efforts.

DETAILED DESCRIPTION OF EMBODIMENTS

In order to enable a person skilled in the art to better understand the solutions of the present invention, the technical solutions in the embodiments of the present invention are clearly and completely described below with reference to the accompanying drawings in the embodiments of the present invention. Obviously, the described embodiments are merely some embodiments of the present invention, rather than all embodiments. Based on the embodiments of the present invention, all other embodiments obtained by a person of ordinary skill in the art without creative efforts shall fall within the scope of protection of the present invention.

It should be noted that the terms "first", "second", etc. in the description and claims of the present invention and the drawings are used to distinguish similar objects and are not necessarily used to describe a specific order or sequence. It should be understood that the data so used are interchangeable under appropriate circumstances, so that the embodiments of the present invention described herein are capable of being practiced in orders other than those illustrated or described herein. Furthermore, the terms "comprising" and "having" and any variations thereof are intended to cover non-exclusive inclusions, for example, processes, methods, apparatuses, products or devices that comprise a series of steps or units need not be limited to those explicitly listed, and may include other steps or elements not expressly listed or inherent to the processes, methods, products or devices.

Figure 1:
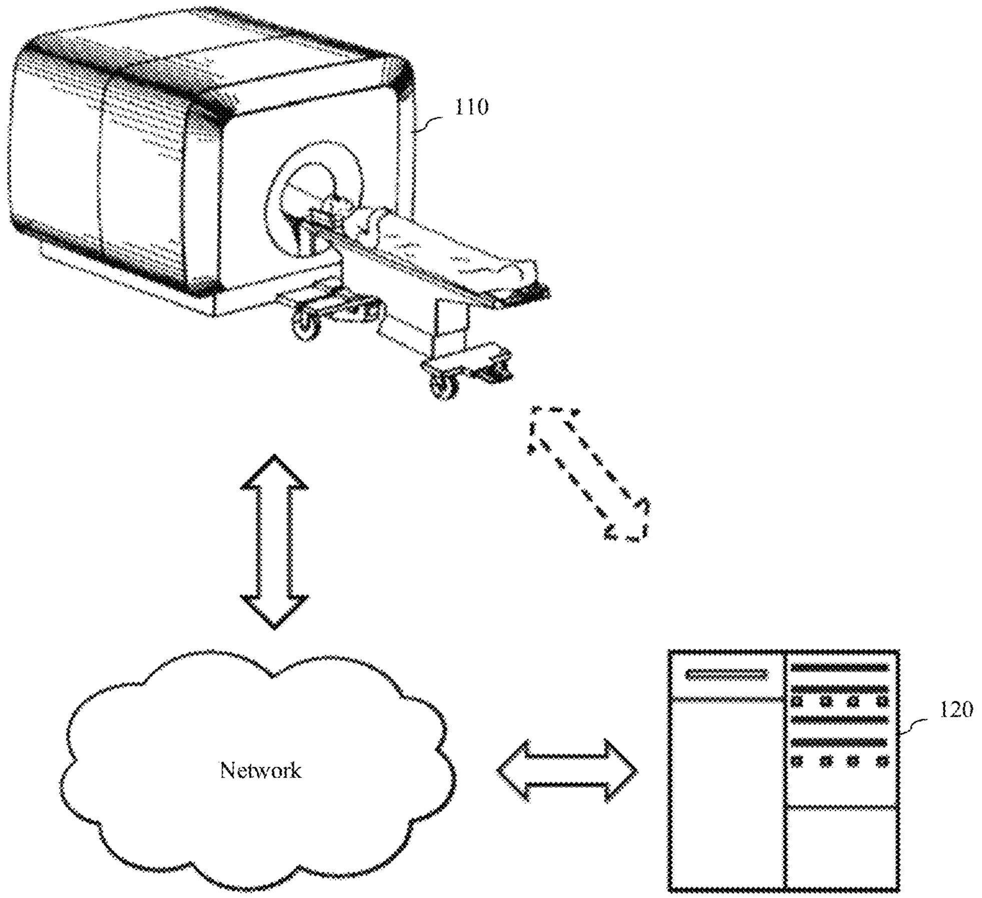
FIG. 1 is a schematic diagram of an implementation environment according to an embodiment of the present invention.

Referring to FIG. 1 of the description, FIG. 1 is a schematic diagram of an implementation environment according to an embodiment of the present invention. As shown in FIG. 1, the implementation environment may include at least one medical scanning device 110 and a computer device 120. The computer device 120 and each medical scanning device 110 may be connected directly or indirectly through wired or wireless communication. This is not limited in the embodiment of the present invention.

The computer device 120 may be, but is not limited to, various servers, personal computers, laptops, smart phones, tablets and portable wearable devices. The server may be an independent server or a server cluster or a distribution system composed of multiple servers, or may be a cloud server that provides a cloud service, a cloud database, cloud computing, a cloud function, cloud storage, a network service, cloud communication, a middleware service, a domain name service, a security service, a content delivery network (Content Delivery Network, CDN), and a basic cloud computing service such as big data and an artificial intelligence platform.

The medical scanning device 110 can use imaging technologies such as OCT imaging and IVUS imaging to obtain an intravascular image comprising a blood vessel segment of interest, and can use imaging technologies such as X-ray angiography and CT imaging to obtain an extravascular image comprising a blood vessel segment to be detected (the blood vessel segment to be detected at least partially coincides with the blood vessel segment of interest).

The computer device 120 can obtain the intravascular image and the extravascular image collected by the medical scanning device 110, and can determine a target fractional flow reserve based on multi-modal medical image by using the method provided by the embodiment of the present invention for doctors to review and provide timely guidance on taking measures. The calculation of the fractional flow reserve is optimized based on multi-modal medical image, so that the target fractional flow reserve that has both blood vessel segment integrity and local accuracy can be obtained, and accuracy and stability of the fractional flow reserve calculated based on multi-modal medical image are higher than that of a fractional flow reserve calculated based on single medical imaging.

Specifically, the FFR determination method based on multi-modal medical image provided by the embodiment of the present invention can be applied to a scenario of calculating the fractional flow reserve based on extravascular images and intravascular images of coronary arteries, such as the left circumflex coronary artery, left anterior descending coronary artery, and right coronary artery.

It should be noted that FIG. 1 is only an example. The person skilled in the art can understand that, although only one medical scanning device 110 is shown in FIG. 1, this does not limit the embodiment of the present invention, and more or fewer medical scanning devices 110 may be included than shown in the figure.

Figure 2:
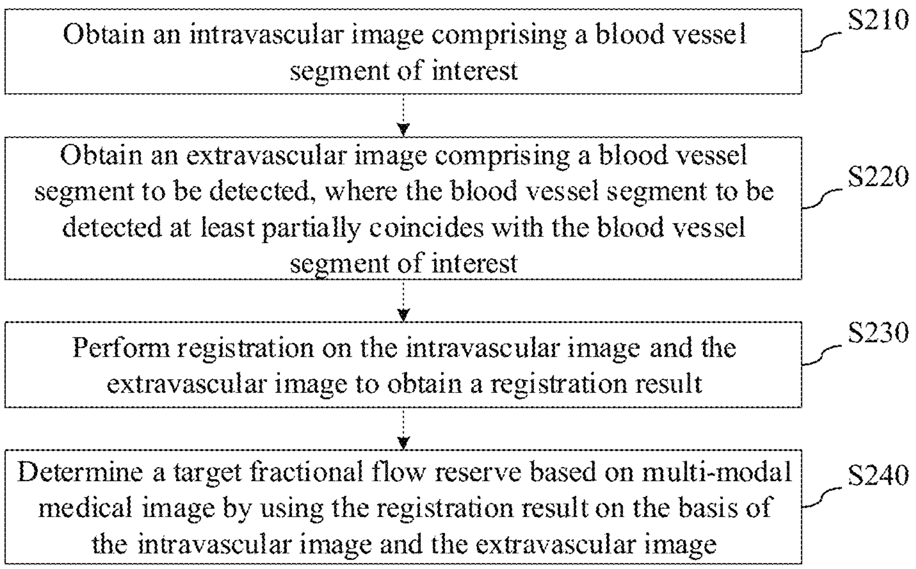
FIG. 2 is a flowchart of an FFR determination method based on multi-modal medical image according to an embodiment of the present invention.

Referring to FIG. 2 of the description, FIG. 2 is a flow of an FFR determination method based on multi-modal medical image according to an embodiment of the present invention. This method can be applied to the computer device 120 in FIG. 1. Specifically, as shown in FIG. 2, the method may include the following steps:

S210: Obtain an intravascular image comprising a blood vessel segment of interest.

In the embodiment of the present invention, the blood vessel segment of interest may be a certain blood vessel segment that is abnormal relative to a normal blood vessel. Obtaining an intravascular image may be directly obtaining an image that is separated and includes only the blood vessel segment of interest, or the intravascular image may be an image that is corresponding to the blood vessel segment of interest and that is selected from an intravascular image of a blood vessel segment, and this is not limited in the embodiment of the present invention. If a part of the intravascular image has poor imaging quality, only a part of the intravascular image with good imaging quality can be selected for subsequent processing, and a blood vessel segment in the part of the intravascular image with good imaging quality can be used as the blood vessel segment of interest.

In the embodiment of the present invention, the intravascular image may be one type of intravascular image, or may include multiple types of intravascular images. The intravascular image may be directly imported related data, or may be obtained from other resource libraries through real-time configuration connections, or may be obtained from a stored image database after searching based on a name and other information of a user. This is not limited in the embodiment of the present invention. Specifically, the intravascular image may be an OCT image, an IVUS image, or the like.

S220: Obtain an extravascular image comprising a blood vessel segment to be detected, where the blood vessel segment to be detected at least partially coincides with the blood vessel segment of interest.

In the embodiment of the present invention, obtaining an extravascular image may be directly obtaining an image that is separated and that includes only the blood vessel segment to be detected, or the extravascular image may be an image that is corresponding to the blood vessel segment to be detected and that is selected from the extravascular image of the blood vessel segment to be detected, and this is not limited in the embodiment of the present invention. If a part of the extravascular image has poor imaging quality, only a part of the extravascular image with good imaging quality can be selected for subsequent processing, and a blood vessel segment in the part of the extravascular image with good imaging quality can be used as the blood vessel segments to be detected.

In the embodiment of the present invention, the extravascular image may be one type of extravascular image, or may include multiple types of extravascular images. The extravascular image may be directly imported relevant data, or may be obtained from other resource libraries through real-time configuration connections, or may be obtained from a stored image database after searching based on a name and other information of a user, and this is not limited in the embodiment of the present invention. Specifically, the extravascular image may be an X-ray image, a CT image, or the like.

In the embodiment of the present invention, the blood vessel segment to be detected may include the blood vessel segment of interest. For example, the blood vessel segment to be detected may be an entire blood vessel in which the blood vessel segment of interest is located, or the blood vessel segment to be detected may include only a part of the blood vessel segment of interest. For example, the blood vessel segment to be detected may include only a part of the blood vessel segment at the proximal, middle or distal end of the blood vessel segment of interest. This is not limited in the embodiment of the present invention.

In practical applications, because the blood vessel presented in the extravascular image is often relatively complete, the blood vessel segment of interest is generally corresponding to a part of the blood vessel segment to be detected. When the blood vessel segment of interest exceeds the range of the blood vessel segment to be detected, the blood vessel segment of interest can be cut according to the actual situation, to obtain a fractional flow reserve that is based on multi-modal medical image and that is corresponding to the blood vessel segment to be detected, or the blood vessel segment of interest can be used to extend the blood vessel segment to be detected, to obtain a fractional flow reserve that is based on multi-modal medical image and that is corresponding to the extended blood vessel segment.

S230: Perform registration on the intravascular image and the extravascular image to obtain a registration result.

In the embodiment of the present invention, registration can be performed based on feature information of the intravascular image and feature information of the extravascular image, to obtain a corresponding relationship between the blood vessel segment of interest and the blood vessel segment to be detected.

In the embodiment of the present invention, the perform registration on the intravascular image and the extravascular image to obtain a registration result may include:

obtaining a first feature information of the blood vessel segment of interest in the intravascular image, where the first feature information includes internal lumen information of the blood vessel segment of interest;

obtaining a second feature information of the blood vessel segment to be detected in the extravascular image, where the second feature information includes external lumen information of the blood vessel segment to be detected; and performing registration based on the first feature information and the second feature information to obtain a registration result.

Specifically, image processing can be performed on the intravascular image and the extravascular image respectively to obtain corresponding first feature information and second feature information. The internal lumen information may include an internal blood vessel diameter and an internal blood vessel length at each point in the blood vessel. The internal blood vessel diameter refers to a blood vessel diameter obtained based on the intravascular image, and the internal blood vessel length is a length along an axis of the blood vessel from a certain point on the internal lumen of the blood vessel to a proximal endpoint of the blood vessel segment of interest. The external lumen information may include an external blood vessel diameter and an external blood vessel length at each point outside the blood vessel. The external blood vessel diameter refers to a blood vessel diameter obtained based on the extravascular image. The external blood vessel length is a certain value a length along an axis of the blood vessel from a certain point on the external lumen of the blood vessel to a proximal endpoint of the blood vessel segment to be detected.

Optionally, the first feature information may include branch opening information, histological information, or vascular plaque information of the blood vessel segment of interest, and the second feature information may include branch information or stress information of the blood vessel segment to be detected. The branch opening information may include a serial number of an internal branch blood vessel (the serial number includes information about which branch on the blood vessel the branch belongs to) and position information of the internal branch blood vessel relative to the blood vessel segment of interest. The branch information may include a serial number of an external branch blood vessel (the serial number includes information about which branch of the blood vessel the branch belongs to) and position information of the external branch blood vessel relative to the blood vessel segment to be detected.

It should be noted that, in the embodiment of the present invention, image processing can be performed on the intravascular image and the extravascular image by using various image processing methods in the prior art to obtain corresponding first feature information and second feature information. Different feature information can also be obtained through different image processing methods. This is not limited in the embodiment of the present invention. For example, lumen segmentation can be performed on the intravascular image and the extravascular image by using various lumen segmentation methods in the prior art, such as an artificial intelligence-based lumen segmentation method, to respectively obtain corresponding external lumen information and internal lumen information. Branch identification can be performed on the intravascular image and the extravascular image by using various branch identification methods in the prior art (such as an artificial intelligence-based branch identification method), to respectively obtain corresponding branch opening information and branch information.

Specifically, when performing registration, primary registration can be first performed on the first feature information and the second feature information, to obtain third feature information, and then secondary registration can be performed on the first feature information and the third feature information, to obtain a registration result. The third feature information includes external lumen information of a first target blood vessel segment corresponding to the blood vessel segment of interest in the extravascular image, and the registration result may be a corresponding relationship between the first feature information and the third feature information. It should be noted that, in the embodiment of the present invention, the blood vessel segment of interest is located inside the blood vessel, and the first target blood vessel segment refers to a blood vessel segment that is located outside the blood vessel and that is corresponding to the blood vessel segment of interest.

It should be noted that, in the embodiment of the present invention, the sequence of the step of obtaining a first feature information of the blood vessel segment of interest and the sequence of the step of obtaining a second feature information of the blood vessel segment to be detected can be exchanged, or the steps can be performed at the same time. The sequence in which the first feature information of the blood vessel segment of interest and the second feature information of the blood vessel segment to be detected are obtained is not limited in the embodiment of the present invention.

It should be noted that, in some possible embodiments, registration may be performed on the intravascular image and the extravascular image by using other registration methods in the prior art. This is not limited in the embodiment of the present invention.

S240: Determine a target fractional flow reserve based on multi-modal medical image by using the registration result on the basis of the intravascular image and the extravascular image.

In the embodiment of the present invention, the target fractional flow reserve may be a fractional flow reserve corresponding to the blood vessel segment to be detected, or may be a fractional flow reserve corresponding to an extended blood vessel segment obtained by extending the blood vessel segment to be detected by using the blood vessel segment of interest. The target fractional flow reserve can express a complete blood vessel segment and has good local accuracy. Accuracy and stability of the fractional flow reserve calculated based on multi-modal medical image are higher than that of a fractional flow reserve calculated based on single medical imaging, and this can help doctors better evaluate a blood supply function of the blood vessel, and accurately determine the location of the stenosis of the blood vessel.

Figure 3:
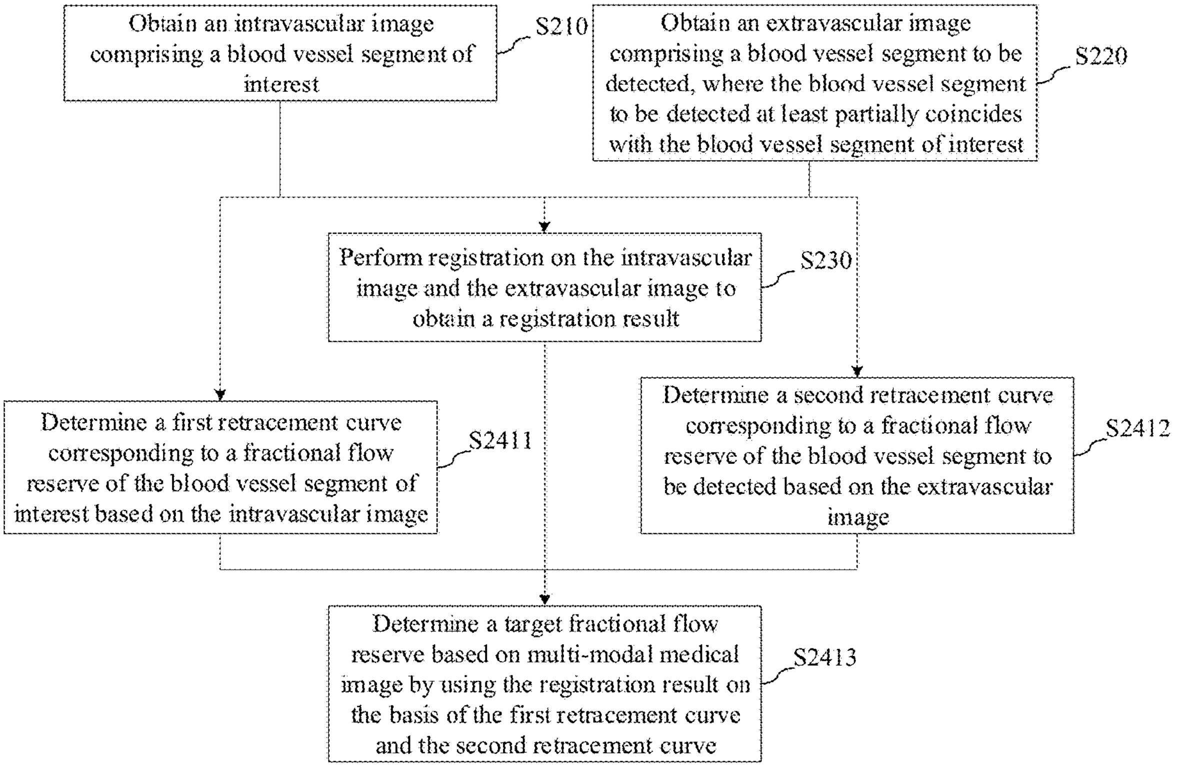
FIG. 3 is a flowchart of an FFR determination method based on multi-modal medical image according to another embodiment of the present invention.

In the embodiment of the present invention, with reference to FIG. 3 of the description, the determine a target fractional flow reserve based on multi-modal medical image by using the registration result on the basis of the intravascular image and the extravascular image may include the following steps:

S2411: Determine a first retracement curve corresponding to a fractional flow reserve of the blood vessel segment of interest based on the intravascular image.

The first retracement curve is a relationship curve between a blood vessel position in the blood vessel segment of interest and the fractional flow reserve. In the embodiment of the present invention, various methods for determining the fractional flow reserve based on the intravascular image in the prior art can be used to calculate the fractional flow reserve, to obtain the first retracement curve. This is not limited in the embodiment of the present invention. For example, feature information such as internal lumen information and branch opening information of the blood vessel segment of interest can be obtained from the intravascular image, a first blood vessel lumen model can be reconstructed, and fluid dynamics analysis can be performed based on a normal blood flow velocity to calculate the fractional flow reserve, to obtain the first retracement curve. The normal blood flow velocity can be predetermined.

In a possible embodiment, the determine a first retracement curve corresponding to a fractional flow reserve of the blood vessel segment of interest based on the intravascular image may include:

obtaining a blood flow velocity of the blood vessel segment to be detected; and determining a first retracement curve corresponding to a fractional flow reserve of the blood vessel segment of interest based on the intravascular image and the blood flow velocity.

Specifically, the blood flow velocity of the blood vessel segment to be detected can be calculated based on the extravascular image. The specific calculation method is the prior art, and details are not described herein again in the embodiment of the present invention. For example, the blood flow velocity of the blood vessel segment to be detected can be measured by the angiography technology. For example, a flow velocity of a contrast agent in the blood vessel segment to be detected can be measured as the blood flow velocity of the blood vessel segment to be detected. Alternatively, based on an angiographic image sequence of the blood vessel segment to be detected, an average blood flow velocity during the filling process of the contrast agent is calculated as the blood flow velocity of the blood vessel segment to be detected. It should be noted that, in some possible embodiments, the blood flow velocity of the blood vessel segment to be detected can be obtained by using other blood flow velocity calculation methods in the prior art. This is not limited in the embodiment of the present invention.

Specifically, after obtaining the blood flow velocity of the blood vessel segment to be detected, a calculation process of calculating the fractional flow reserve based on the intravascular image can be optimized by using the blood flow velocity, so that a fractional flow reserve and a first retracement curve having higher accuracy are obtained.

In another possible embodiment, the determine a first retracement curve corresponding to a fractional flow reserve of the blood vessel segment of interest based on the intravascular image may include:

obtaining a first branch blood vessel information of the blood vessel segment of interest, where the first branch blood vessel information includes branch opening information obtained based on the intravascular image, and branch information obtained based on the extravascular image; and determining a first retracement curve corresponding to a fractional flow reserve of the blood vessel segment of interest based on the intravascular image and the first branch blood vessel information.

Specifically, various branch identification methods in the prior art (such as an artificial intelligence-based branch identification method) can be used to perform branch identification on the intravascular image to obtain the branch opening information of the blood vessel segment of interest, and perform branch identification on the extravascular image to obtain branch information of the blood vessel segment to be detected, and then branch information of the blood vessel segment that is corresponding to the blood vessel segment of interest and that is in the blood vessel segment to be detected is determined as the branch information of the blood vessel segment of interest by using the registration information. After obtaining the first branch blood vessel information of the blood vessel segment of interest, the first branch blood vessel information can be used to optimize a calculation process of calculating the fractional flow reserve based on the intravascular image, so that a fractional flow reserve and a first retracement curve having higher accuracy are obtained. For example, a process of reconstructing a first blood vessel lumen model can be optimized by using the first branch blood vessel information.

In another possible embodiment, the blood flow velocity of the blood vessel segment to be detected and the first branch blood vessel information of the blood vessel segment of interest can also be used to simultaneously optimize the calculation process of calculating the fractional flow reserve based on the intravascular image, so that a fractional flow reserve and a first retracement curve having higher accuracy are obtained. For example, the first branch blood vessel information can be used to optimize the process of reconstructing the first blood vessel lumen model, and fluid dynamics analysis can be performed based on the blood flow velocity of the blood vessel segment to be detected to calculate the fractional flow reserve, to obtain the first retracement curve.

S2412: Determine a second retracement curve corresponding to a fractional flow reserve of the blood vessel segment to be detected based on the extravascular image.

The second retracement curve is a relationship curve between a blood vessel position in the blood vessel segment to be detected and the fractional flow reserve. In the embodiment of the present invention, various methods for determining a fractional flow reserve based on an extravascular image in the prior art can be used to calculate the fractional flow reserve to obtain the second retracement curve. This is not limited in the embodiment of the present invention. For example, feature information such as external lumen information and branch information of the blood vessel segment to be detected can be obtained from the extravascular image, a second blood vessel lumen model can be reconstructed, and fluid dynamics can be performed based on a normal blood flow velocity to calculate the fractional flow reserve, to obtain the second retracement curve. The normal blood flow velocity can be predetermined.

In a possible embodiment, the determine a second retracement curve corresponding to a fractional flow reserve of the blood vessel segment to be detected based on the extravascular image may include:

obtaining a blood flow velocity of the blood vessel segment to be detected; and determining a second retracement curve corresponding to a fractional flow reserve of the blood vessel segment to be detected based on the extravascular image and the blood flow velocity.

Specifically, the method for determining the blood flow velocity of the blood vessel segment to be detected is similar to that in step S2411, and details are not described herein again in the embodiment of the present invention. After obtaining the blood flow velocity of the blood vessel segment to be detected, the blood flow velocity can be used to optimize the calculation process of calculating the fractional flow reserve based on the extravascular image, so that a fractional flow reserve and a second retracement curve having higher accuracy are obtained.

In another possible embodiment, the determine a second retracement curve corresponding to a fractional flow reserve of the blood vessel segment to be detected based on the extravascular image may include:

- obtaining a second branch blood vessel information of the blood vessel segment to be detected, where the second branch blood vessel information comprises branch opening information obtained based on the intravascular image, and branch information obtained based on the extravascular image; and
- determining a second retracement curve corresponding to a fractional flow reserve of the blood vessel segment to be detected based on the extravascular image and the second branch blood vessel information.

Specifically, various branch identification methods in the prior art (such as an artificial intelligence-based branch identification method) can be used to perform branch identification on the extravascular image to obtain the branch information of the blood vessel segment to be detected, and perform branch identification on the intravascular image to obtain the branch opening information of the blood vessel segment of interest, and then branch opening information of a blood vessel segment that is corresponding to the blood vessel segment to be detected and that is in the blood vessel segment of interest is determined as the branch opening information of the blood vessel segment to be detected by using the registration information. After obtaining the second branch blood vessel information of the blood vessel segment to be detected, the second branch blood vessel information can be used to optimize the calculation process of calculating the fractional flow reserve based on the extravascular image, so that a fractional flow reserve and a second retracement curve having higher accuracy are obtained. For example, the second branch blood vessel information may be used to optimize the process of reconstructing a second blood vessel lumen model.

In another possible embodiment, the blood flow velocity of the blood vessel segment to be detected and the second branch blood vessel information of the blood vessel segment to be detected can be used to simultaneously optimize the calculation process of calculating the fractional flow reserve based on the extravascular image, so that a fractional flow reserve and a second retracement curve having higher accuracy are obtained. For example, the second branch blood vessel information can be used to optimize the process of reconstructing a second blood vessel lumen model, and fluid dynamics analysis can be performed based on the blood flow velocity of the blood vessel segment to be detected to calculate the fractional flow reserve, to obtain the second retracement curve.

S2413: Determine a target fractional flow reserve based on multi-modal medical image by using the registration result on the basis of the first retracement curve and the second retracement curve.

Because the fractional flow reserve calculated based on the intravascular image has good local accuracy, the fractional flow reserve calculated based on the extravascular image can express the complete blood vessel segment, the fractional flow reserve calculated based on the intravascular image can be fused with the fractional flow reserve calculated based on the extravascular image, to obtain a target fractional flow reserve that has both integrity of the blood vessel segment and local accuracy.

In the embodiment of the present invention, the determine a target fractional flow reserve based on multi-modal medical image by using the registration result on the basis of the first retracement curve and the second retracement curve may include:

- determining a first fractional flow reserve sequence based on the first retracement curve, where the first fractional flow reserve sequence is corresponding to a first blood vessel position sequence of the blood vessel segment of interest in the intravascular image;
- determining a second fractional flow reserve sequence based on the second retracement curve, where the second fractional flow reserve sequence is corresponding to a second blood vessel position sequence of the blood vessel segment to be detected in the extravascular image, and the second blood vessel position sequence at least partially coincides with the first blood vessel position sequence;
- fusing the first fractional flow reserve sequence and the second fractional flow reserve sequence by using the registration result, to obtain a target fractional flow reserve sequence; and
- determining a target fractional flow reserve based on multi-modal medical image on the basis of the target fractional flow reserve sequence.

In practical applications, in the extravascular image, starting from a proximal end of the blood vessel segment to be detected, uniform sampling can be performed on the external lumen of the blood vessel segment to be detected, to obtain the second blood vessel position sequence of the blood vessel segment to be detected, and determine the fractional flow reserve of the blood vessel segment to be detected corresponding to each blood vessel position in the second blood vessel position sequence based on the second retracement curve, to obtain the second fractional flow reserve sequence. Then, a blood vessel position subsequence located in a first target blood vessel segment corresponding to the blood vessel segment of interest in the second blood vessel position sequence may be determined, and the blood vessel position subsequence may be used as a subsequence of the first blood vessel position sequence. For the part of the blood vessel segment of interest that exceeds the range of the blood vessel segment to be detected, uniform sampling can be performed at the same sampling interval, and the first blood vessel position sequence can be obtained. Then, the fractional flow reserve of the blood vessel segment of interest corresponding to each blood vessel position in the first blood vessel position sequence is determined by using the registration result based on the first retracement curve, to obtain the first fractional flow reserve sequence.

It should be noted that, during the sampling process, in a preferred embodiment, a proximal endpoint of the blood vessel segment to be detected is used as a first sampling position, a distal endpoint of the blood vessel segment to be detected is used as a last sampling position, and a proximal endpoint and a distal endpoint of the blood vessel segment of interest are also included in the second blood vessel position sequence. However, the above preferred embodiment does not limit the sampling position. In actual applications, the second blood vessel position sequence may include the proximal endpoint and the distal endpoint of the blood vessel segment to be detected, as well as one or more positions of the proximal endpoint and the distal endpoint of the blood vessel segment of interest, or may not include any one of the positions. This is not limited in the embodiment of the present invention.

Specifically, the fusing the first fractional flow reserve sequence and the second fractional flow reserve sequence by using the registration result, to obtain a target fractional flow reserve sequence includes:

- calculating a first difference sequence based on the first fractional flow reserve sequence, where a value in the first difference sequence is a decrease value of a fractional flow reserve of a corresponding position relative to a fractional flow reserve of a previous position in the first fractional flow reserve sequence;
- calculating a second difference sequence based on the second fractional flow reserve sequence, where a value in the second difference sequence is a decrease value of a fractional flow reserve of a corresponding position relative to a fractional flow reserve of a previous position in the second fractional flow reserve sequence;
- fusing the first difference sequence and the second difference sequence by using the registration result to obtain a target difference sequence; and
- determining the target fractional flow reserve sequence based on the target difference sequence.

In practical applications, because the blood vessel segment to be detected at least partially coincides with the blood vessel segment of interest, the following cases may occur in practical applications:

In a first case, the blood vessel segment of interest is a part of the blood vessel segment to be detected. At this time, the fusing the first difference sequence and the second difference sequence by using the registration result to obtain a target difference sequence may include: determining a target subsequence that is in the second difference sequence and that is corresponding to the first difference sequence by using the registration result; and replacing the target subsequence in the second difference sequence with the first difference sequence, to obtain the target difference sequence.

Figure 4:
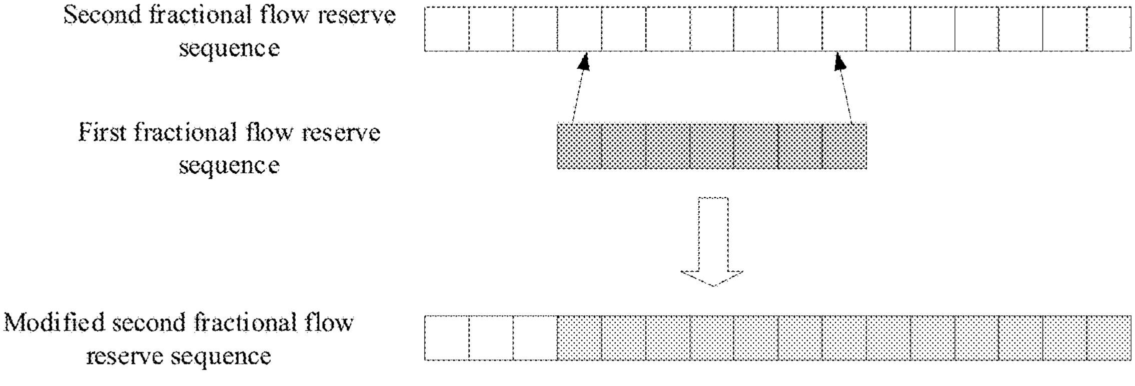
FIG. 4 is a schematic diagram of determining a target fractional flow reserve sequence according to an embodiment of the present invention.

For example, with reference to FIG. 4 of the description, assuming that the first fractional flow reserve sequence determined based on the first retracement curve is {1, 0.99, 0.98, 0.97}, and the second fractional flow reserve sequence determined based on the second retracement curve is {1, 0.98, 0.96, 0.94, 0.92, 0.90, 0.88, 0.86, 0.84, 0.82, 0.80}, then:

In a first step, the first difference sequence can be calculated as {0, 0.01, 0.01, 0.01}, and the second difference sequence is {0, 0.02, 0.02, 0.02, 0.02, 0.02, 0.02, 0.02, 0.02, 0.02, 0.02}.

In a second step, it can be determined according to the registration result that a target subsequence that is in the second difference sequence and that is corresponding to the first difference sequence is a subsequence consisting of the third sequence value to the sixth sequence value {0.02, 0.02, 0.02, 0.02}, then the target subsequence is replaced with the first difference sequence to obtain the target difference sequence {0, 0.02, 0, 0.01, 0.01, 0.01, 0.02, 0.02, 0.02, 0.02, 0.02}.

In a second case, the blood vessel segment to be detected includes only a part of the blood vessel segment at a proximal end or a distal end of the blood vessel segment of interest. In this case, the fusing the first difference sequence and the second difference sequence by using the registration result to obtain a target difference sequence may include: determining a first subsequence that is in the first difference sequence and that is corresponding to the second difference sequence by using the registration result, and a second subsequence that is in the second difference sequence and that is corresponding to the first difference sequence; and replacing the second subsequence in the second difference sequence with the first subsequence, to obtain the target difference sequence.

Optionally, after replacing the second subsequence in the second difference sequence with the first subsequence, a difference sequence in the first difference sequence other than the first subsequence can be added to the difference sequence obtained by replacement. Finally, the target difference sequence is obtained.

For example, assuming that the first difference sequence is calculated as {0, 0.01, 0.01, 0.01} and the second difference sequence is {0, 0.02, 0.02, 0.02, 0.02, 0.02, 0.02, 0.02, 0.02, 0.02, 0.02}, according to the registration result, it is determined that a first subsequence that is in the first difference sequence and that is corresponding to the second difference sequence is a subsequence consisting of the third sequence value to the fourth sequence value {0.01, 0.01}, a second subsequence that is in the second difference sequence and that is corresponding to the first difference sequence is a subsequence consisting of the first sequence value to the second sequence value {0, 0.02}, then the second subsequence in the second difference sequence is replaced with the first subsequence, to obtain the target difference sequence {0.01, 0.01, 0.02, 0.02, 0.02, 0.02, 0.02, 0.02, 0.02, 0.02, 0.02}.

Optionally, the difference sequence {0, 0.01} in the first difference sequence other than the first subsequence can also be added to the difference sequence obtained by replacement, and finally the target difference sequence {0, 0.01, 0.01, 0.01, 0.02, 0.02, 0.02, 0.02, 0.02, 0.02, 0.02, 0.02, 0.02} is obtained.

In a third case, the blood vessel segment to be detected is a part of the blood vessel segment of interest. At this time, the fusing the first difference sequence and the second difference sequence by using the registration result to obtain a target difference sequence may include: determining a target subsequence that is in the first difference sequence and that is corresponding to the second difference sequence by using the registration result; and replacing the target subsequence in the first difference sequence with the second difference sequence to obtain the target difference sequence.

In a fourth case, the blood vessel segment to be detected and the blood vessel segment of interest are the same blood vessel segment. At this time, the fusing the first difference sequence and the second difference sequence by using the registration result to obtain a target difference sequence may include: performing averaging or weighted averaging on two differences corresponding to a position in the first difference sequence and a position in the second difference sequence to obtain a target difference corresponding to the position, and finally obtain the target difference sequence.

For example, assuming that the first difference sequence is {0, 0.01, 0.01, 0.01}, and the second difference sequence is {0, 0.02, 0.02, 0.02}, averaging may be performed on two differences corresponding to a position in the first difference sequence and a position in the second difference sequence, to obtain the target difference sequence {0, 0.015, 0.015, 0.015}.

It should be noted that, in some possible embodiments, in the first to third cases, for the parts corresponding to the positions in the first difference sequence and the second difference sequence, a method such as averaging or weighted averaging can also be used to obtain the target difference corresponding to each position. This is not limited in the embodiment of the present invention.

In practical applications, the determining the target fractional flow reserve sequence according to the target difference sequence may include: subtracting a sum of the sequence values before the current position (including the current position) in the target difference sequence from a fractional flow reserve of a first position in the second fractional flow reserve sequence, to obtain a fractional flow reserve corresponding to the current position, and finally obtain the target fractional flow reserve sequence.

For example, assuming that the target difference sequence is {0, 0.02, 0, 0.01, 0.01, 0.01, 0.02, 0.02, 0.02, 0.02, 0.02}, then a fractional flow reserve of a first position is 1−0=1, a fractional flow reserve of a second position is 1−0−0.02=0.98, a fractional flow reserve of a third position is 1−0−0.02−0=0.98, and a fractional flow reserve of a fourth position is 1−0−0.02−0−0.01=0.97. By analogy, the final target fractional flow reserve sequence can be obtained as {1, 0.98, 0.98, 0.97, 0.96, 0.95, 0.93, 0.91, 0.89, 0.87, 0.85}.

Specifically, the determining the target fractional flow reserve based on the multi-modal medical imaging on the basis of the target fractional flow reserve sequence may include:

- performing curve fitting by using the target fractional flow reserve sequence, to obtain a target retracement curve based on multi-modal medical image, where the target retracement curve is a relationship curve between a blood vessel position in a second target blood vessel segment and the fractional flow reserve; and
- using a fractional flow reserve corresponding to the distal endpoint of the second target blood vessel segment in the target retracement curve as the target fractional flow reserve.

The second target blood vessel segment is related to the target fractional flow reserve sequence. For example, when the blood vessel segment of interest is a part of the blood vessel segment to be detected, the second target blood vessel segment is the blood vessel segment to be detected. When the blood vessel segment to be detected includes only a part of the blood vessel segment at a proximal end or a distal end of the blood vessel segment of interest, if the data of the blood vessel segment of interest that exceeds the range of the blood vessel segment to be detected is discarded (that is, when the target fractional flow reserve sequence is calculated, the difference sequence in the first difference sequence other than the first subsequence is not added to the difference sequence obtained by replacement), the second target blood vessel segment is the blood vessel segment to be detected. If the data of the blood vessel segment of interest that exceeds the range of the blood vessel segment to be detected is added (that is, when the target fractional flow reserve sequence is calculated, the difference sequence in the first difference sequence other than the first subsequence is added to the difference sequence obtained by replacement), the second target blood vessel segment is a blood vessel segment obtained by extending the blood vessel segment to be detected by using the blood vessel segment of interest. When the blood vessel segment to be detected is a part of the blood vessel segment of interest, the second target blood vessel segment is the blood vessel segment of interest. When the blood vessel segment to be detected and the blood vessel segment of interest are the same blood vessel segment, the second target blood vessel segment is the blood vessel segment to be detected.

In practical applications, when performing curve fitting, if the target fractional flow reserve sequence does not include a fractional flow reserve (that is 1) corresponding to a proximal endpoint of the second target blood vessel segment, the fractional flow reserve (that is 1) can be first added to the target fractional flow reserve sequence, and then curve fitting is performed, to ensure that the fractional flow reserve corresponding to the proximal endpoint of the second target blood vessel segment is always 1.

In practical applications, when performing sampling on a blood vessel position, if the distal endpoint of the blood vessel segment to be detected is used as the last blood vessel position in the second blood vessel position sequence, and the distal endpoint of the blood vessel segment of interest is used as the last blood vessel position in the first blood vessel position sequence, the fractional flow reserve corresponding to the distal endpoint of the blood vessel segment to be detected or the distal endpoint of the blood vessel segment of interest in the target fractional flow reserve sequence can be directly used as the target fractional flow reserve based on multi-modal medical image.

Figure 5A:
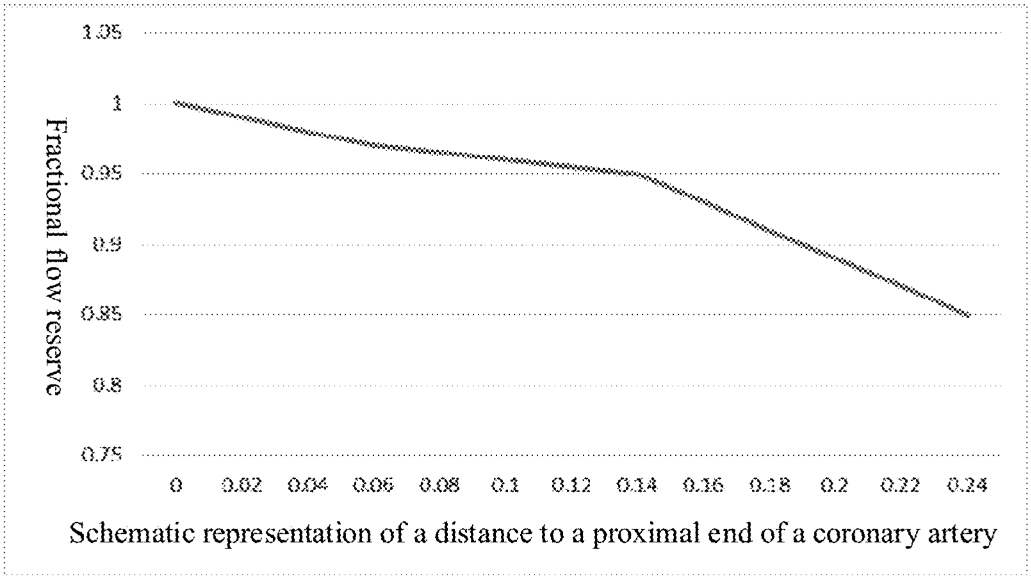
FIG. 5A is a schematic diagram of a first retracement curve according to an embodiment of the present invention.
Figure 5B:
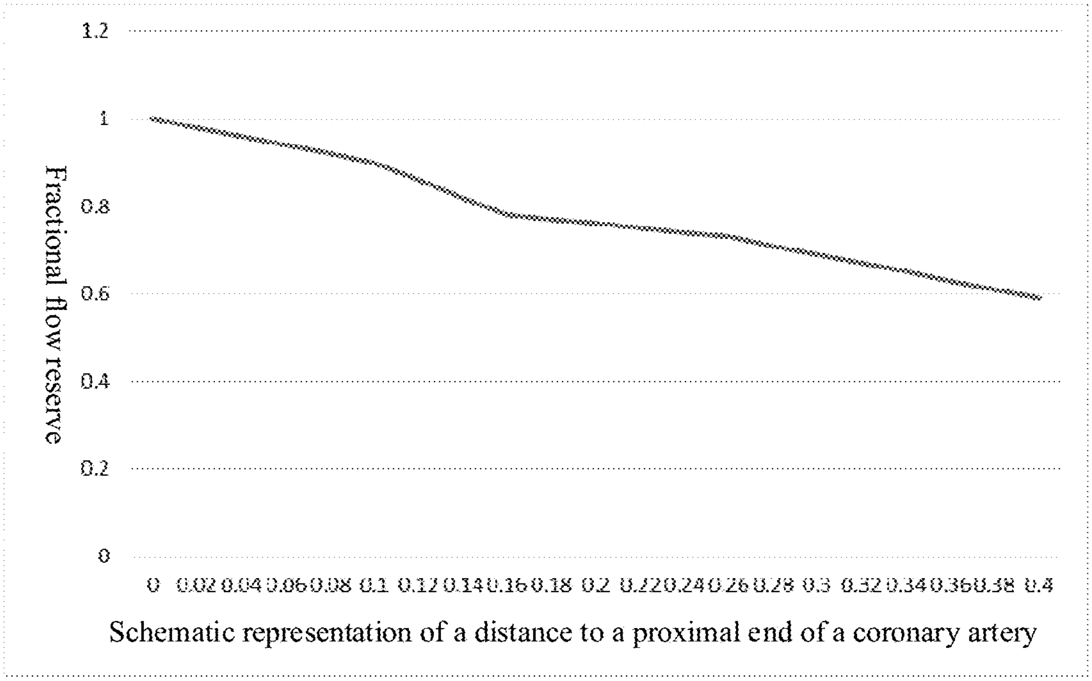
FIG. 5B is a schematic diagram of a second retracement curve according to an embodiment of the present invention.
Figure 5C:
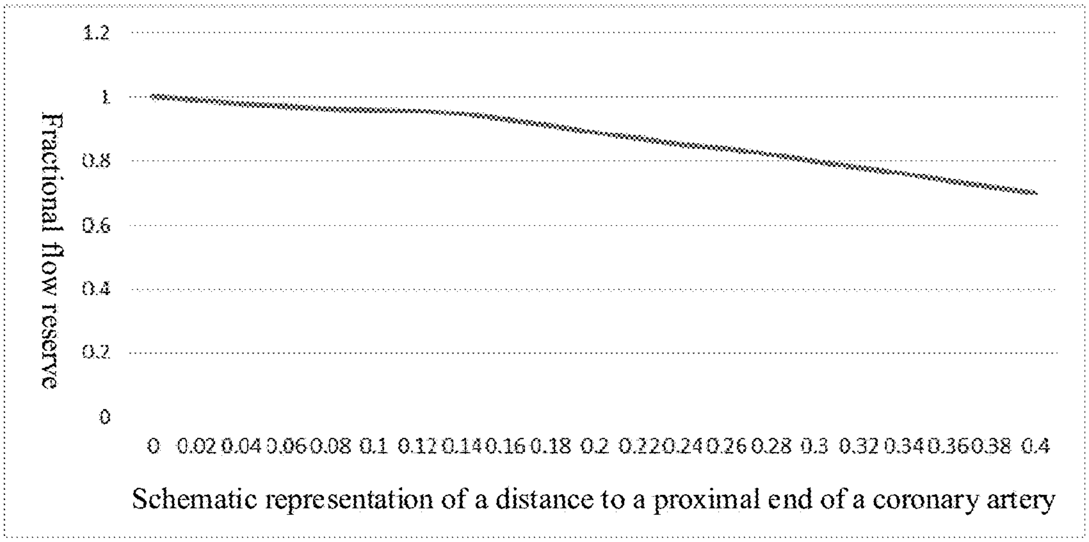
FIG. 5C is a schematic diagram of a target retracement curve according to an embodiment of the present invention.

For example, assuming that the first retracement curve of the blood vessel segment of interest determined according to the intravascular image is shown in FIG. 5A, and the second retracement curve of the blood vessel segment to be detected determined according to the extravascular image is shown in FIG. 5B, the first fractional flow reserve sequence {0.99, 0.98, 0.97, 0.965, 0.96, 0.955, 0.95, 0.93, 0.91, 0.89, 0.87, 0.85} can be determined according to the first retracement curve, the second fractional flow reserve sequence {0.98, 0.96, 0.94, 0.92, 0.9, 0.86, 0.82, 0.78, 0.77, 0.76, 0.75, 0.74, 0.73, 0.71, 0.69, 0.67, 0.65, 0.63, 0.61, 0.59} can be determined according to the second retracement curve, the target fractional flow reserve sequence {0.99, 0.98, 0.97, 0.965, 0.96, 0.955, 0.95, 0.93, 0.91, 0.89, 0.87, 0.85, 0.84, 0.82, 0.8, 0.78, 0.76, 0.74, 0.72, 0.7} can be obtained by using the above method, and the target retracement curve based on multi-modal medical image finally obtained by fitting is shown in FIG. 5C. The target retracement curve can not only express the complete blood vessel segment, but also has higher local accuracy.

The fractional flow reserve corresponding to the last point (that is, the distal endpoint position of the second target blood vessel segment) in the target retracement curve based on multi-modal medical image is the most important, and is a standard for measuring the blood supply of the entire blood vessel and coronary artery. If the fractional flow reserve is greater than 0.8, it indicates that the myocardial blood supply is sufficient, otherwise it indicates that the myocardial blood supply is insufficient. As shown in FIG. 5C, the target fractional flow reserve is 0.7, it indicates that myocardial blood supply is insufficient.

In the embodiment of the present invention, the first retracement curve determined based on the intravascular image and the second retracement curve determined based on the extravascular image are fused, to obtain the target retracement curve and the target fractional flow reserve based on multimodal medical imaging. The fractional flow reserve based on multi-modal medical image not only can express the complete blood vessel segment, but also has higher local accuracy, and accuracy and stability of the fractional flow reserve based on multi-modal medical image are higher than that of the fractional flow reserve calculated based on single medical imaging, so that myocardial ischemia can be more accurately assessed and vascular stenosis can be determined.

Figure 6:
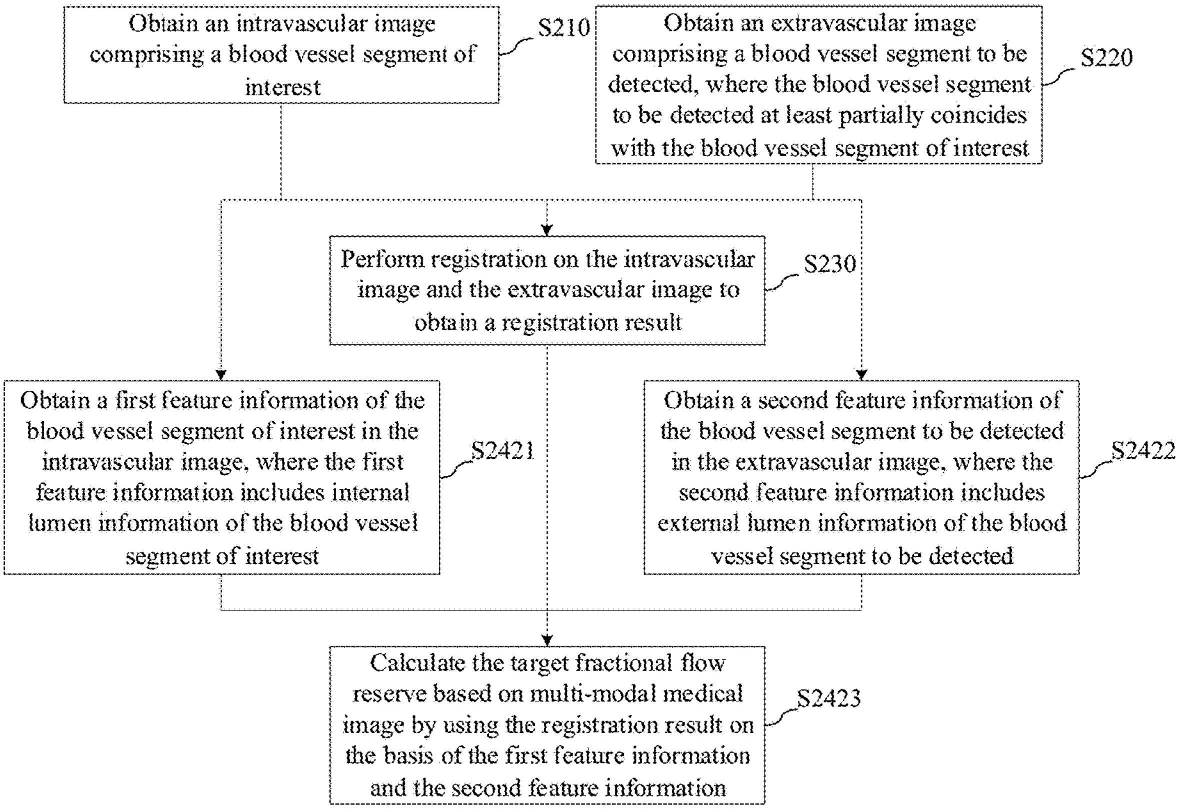
FIG. 6 is a flowchart of an FFR determination method based on multi-modal medical image according to another embodiment of the present invention.

In a possible embodiment, with reference to FIG. 6 of the description, the determine a target fractional flow reserve based on multi-modal medical image by using the registration result on the basis of the intravascular image and the extravascular image may include the following steps:

S2421: Obtain a first feature information of the blood vessel segment of interest in the intravascular image, where the first feature information includes internal lumen information of the blood vessel segment of interest.

S2422: Obtain a second feature information of the blood vessel segment to be detected in the extravascular image, where the second feature information includes external lumen information of the blood vessel segment to be detected.

S2423: Calculate the target fractional flow reserve based on multi-modal medical image by using the registration result on the basis of the first feature information and the second feature information.

Specifically, the first feature information may further include branch opening information, histological information, or vascular plaque information of the blood vessel segment of interest, etc., and the second feature information may further include branch information or stress information of the blood vessel segment to be detected, etc. The method for obtaining the first feature information and the second feature information is similar to that in step S230. Details are not described again in this embodiment of the present invention.

Optionally, a first blood vessel lumen model can be reconstructed based on the first feature information, a second blood vessel lumen model can be reconstructed based on the second feature information, and then the first blood vessel lumen model and the second blood vessel lumen model are fused by using the registration result to obtain a target lumen model, and fluid dynamics analysis is performed based on a blood flow velocity of the blood vessel segment to be detected to calculate a fractional flow reserve, and a corresponding target retracement curve and a target fractional flow reserve based on multi-modal medical image are obtained. The method for determining the blood flow velocity of the blood vessel segment to be detected is similar to step S2411. Details are not described herein again in this embodiment of the present invention.

Optionally, a third blood vessel lumen model can be reconstructed by using the registration result based on the first feature information and the second feature information, and fluid dynamics analysis is performed based on the blood flow velocity of the blood vessel segment to be detected to calculate the fractional flow reserve, and the corresponding target retracement curve and target fractional flow reserve based on multi-modal medical image are obtained. The method for determining the blood flow velocity of the blood vessel segment to be detected is similar to step S2411. Details are not described herein again in this embodiment of the present invention.

Figure 7:
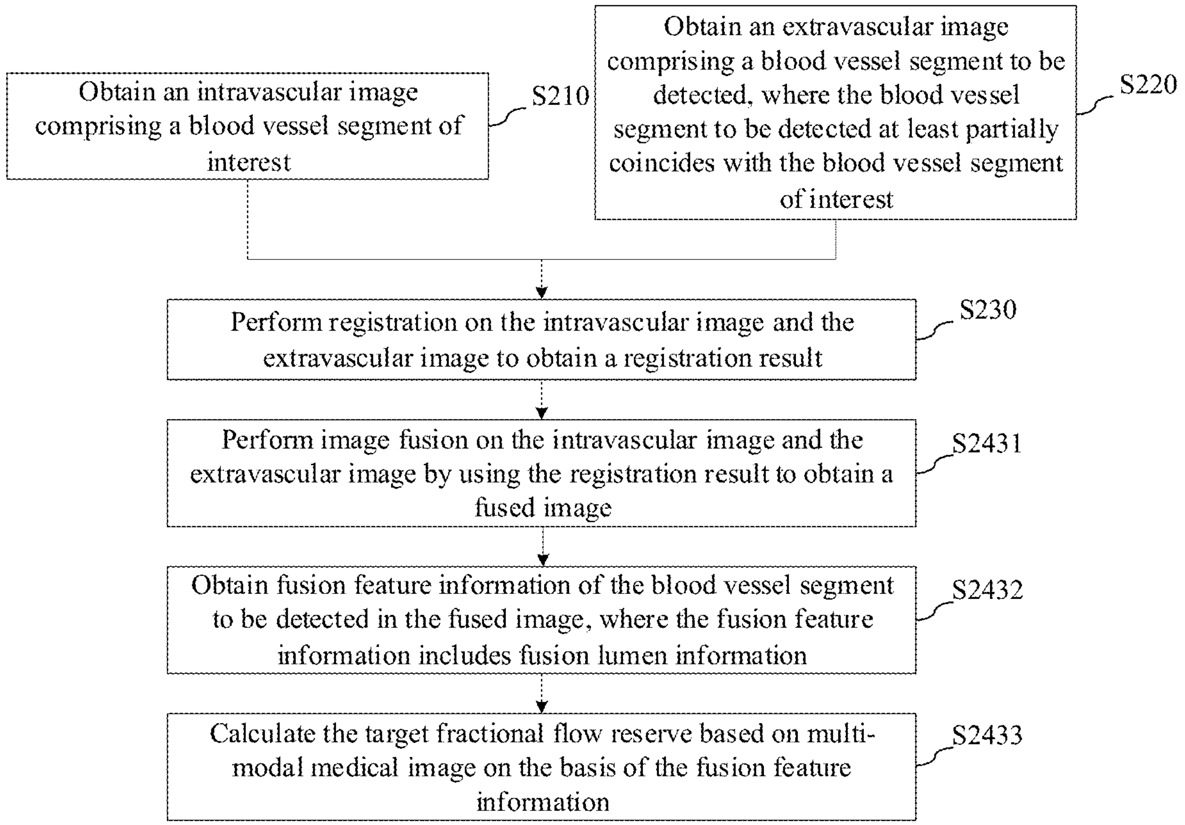
FIG. 7 is a flowchart of an FFR determination method based on multi-modal medical image according to another embodiment of the present invention.

In another possible embodiment, with reference to FIG. 7 of the description, the determine a target fractional flow reserve based on multi-modal medical image by using the registration result on the basis of the intravascular image and the extravascular image includes the following steps:

S2431: Perform image fusion on the intravascular image and the extravascular image by using the registration result to obtain a fused image.

S2432: Obtain fusion feature information of the blood vessel segment to be detected in the fused image, where the fusion feature information includes fusion lumen information.

S2433: Calculate the target fractional flow reserve based on multi-modal medical image on the basis of the fusion feature information.

Specifically, the fusion lumen information may include a blood vessel diameter and a blood vessel length at each point in the blood vessel. The blood vessel diameter refers to a blood vessel diameter obtained based on the fused image, and the blood vessel length is a length along an axis of the blood vessel from a certain point on the blood vessel to a proximal endpoint of the blood vessel in the fused image.

Optionally, the fusion feature information may further include fusion branch information, histological information, or vascular plaque information, etc. The method for obtaining the fusion feature information is similar to that in step S230. Details are not described herein again in this embodiment of the present invention.

Specifically, a fourth blood vessel lumen model can be reconstructed based on the fusion feature information, and fluid dynamics analysis can be performed to calculate the fractional flow reserve based on the blood flow velocity of the blood vessel segment to be detected, to obtain a corresponding target retracement curve and a target fractional flow reserve based on multi-modal medical image. The method for determining the blood flow velocity of the blood vessel segment to be detected is similar to step S2411. Details are not described herein again in this embodiment of the present invention.

In conclusion, according to the FFR determination method based on multi-modal medical image according to the embodiment of the present invention, registration is performed on the intravascular image and the extravascular image, and advantageous information of the intravascular image and the extravascular image can be integrated by using the registration result, to optimize the calculation of the fractional flow reserve, and a fractional flow reserve based on multi-modal medical image that has both integrity of the of blood vessel segment and local accuracy can be obtained, so that accuracy and stability of the calculation of the fractional flow reserve are improved.

In addition, the fractional flow reserve is obtained by calculation by performing fusion based on multiple medical images, and a problem of selection and unification caused by calculating different fractional flow reserves for the same blood vessel based on different medical images can be solved. In addition, in the embodiment of the present invention, the FFR determination method based on multi-modal medical image selects advantageous information of various medical images on blood vessel expression, and accuracy and stability of the fractional flow reserve calculated based on multi-modal medical image are higher than that of a fractional flow reserve calculated based on single medical imaging.

Figure 8:
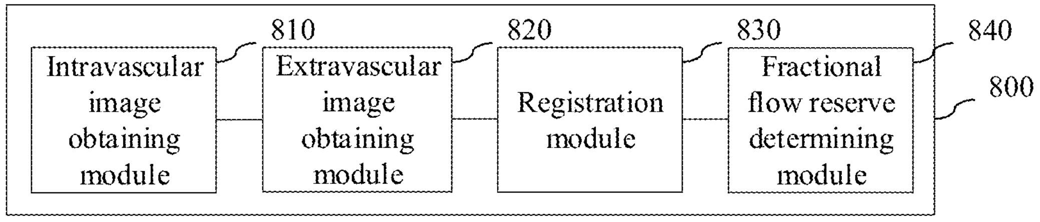
FIG. 8 is a schematic structural diagram of an FFR determination apparatus based on multi-modal medical image according to an embodiment of the present invention.

Referring to FIG. 8 of the description, FIG. 8 is a structure of an FFR determination apparatus 800 based on multi-modal medical image according to an embodiment of the present invention. As shown in FIG. 8, the apparatus 800 may include:

an intravascular image obtaining module 810, configured to obtain an intravascular image comprising a blood vessel segment of interest;

an extravascular image obtaining module 820, configured to obtain an extravascular image comprising a blood vessel segment to be detected, where the blood vessel segment to be detected at least partially coincides with the blood vessel segment of interest;

a registration module 830, configured to perform registration on the intravascular image and the extravascular image to obtain a registration result; and a fractional flow reserve determining module 840, configured to determine a target fractional flow reserve based on multi-modal medical image by using the registration result on the basis of the intravascular image and the extravascular image.

It should be noted that, when the functions of the apparatus provided by the above embodiment are implemented, only the division of the above functional modules is used as an example for description. In practical applications, the above functions can be completed by being allocated to different functional modules according to needs, that is, the internal structure of the device is divided into different functional modules, to complete all or part of the functions described above. In addition, the apparatus provided by the above embodiment and the corresponding method embodiment belong to the same concept, and the specific implementation process can be found in the corresponding method embodiment. Details are not described herein again.

An embodiment of the present invention further provides an electronic device. The electronic device includes a processor and a memory. At least one instruction or at least one program is stored in the memory. The at least one instruction or the at least one program is loaded and executed by the processor to implement the FFR determination method based on multi-modal medical image as provided in the above method embodiment.

The memory can be used to store a computer program and a module, and the processor executes various functional applications and data processing by running the computer program and the module stored in the memory. The memory may mainly include a program storage area and a data storage area. The program storage area may store application programs required for an operating system and a function, etc.; the data storage area may store data created based on the use of the device, etc. In addition, the memory may include a high-speed random access memory and may further include a non-volatile memory, such as at least one magnetic disk storage device, a flash memory device, or another volatile solid-state storage device. Correspondingly, the memory may further include a memory controller to provide the processor with access to the memory.

Figure 9:
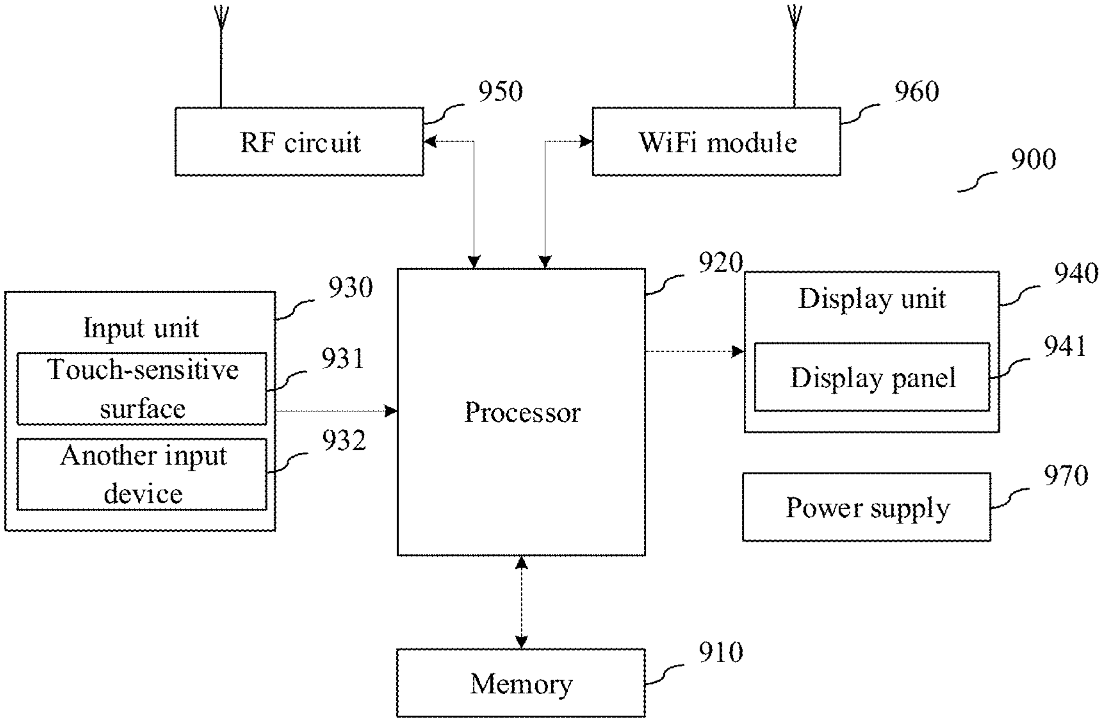
FIG. 9 is a schematic structural diagram of an electronic device according to an embodiment of the present invention.

In a specific embodiment, FIG. 9 is a schematic structural diagram of hardware of an electronic device used to implement the FFR determination method based on multi-modal medical image according to an embodiment of the present invention. The electronic device may be a computer terminal, a mobile terminal, or other equipment, and the electronic device may further participate in constituting or including the FFR determination apparatus based on multi-modal medical image provided by the embodiment of the present invention. As shown in FIG. 9, the electronic device 900 may include components such as a memory 910 of one or more computer-readable storage media, a processor 920 of one or more processing cores, an input unit 930, a display unit 940, a radio frequency (Radio Frequency, RF) circuit 950, Wireless Fidelity (Wireless Fidelity, WiFi) module 960, and a power supply 970. The person skilled in the art can understand that the structure of the electronic device shown in FIG. 9 does not constitute a limitation on the electronic device 900, and may include more or fewer components than shown, or combine certain components, or arrange different components.

The memory 910 can be used to store a software program and a module, and the processor 920 executes various functional applications and data processing by running and executing the software program and the module stored in the memory 910 and calling the data stored in the memory 910. The memory 910 may mainly include a program storage area and a data storage area. The program storage area may store application programs required for an operating system and a function, etc.; the data storage area may store data created based on the use of the electronic device, etc.. In addition, the memory 910 may include a high-speed random access memory, and may further include a non-volatile memory, such as a hard disk, a memory, a plug-in hard disk, a smart media card (Smart Media Card, SMC), a secure digital (Secure Digital, SD) card, a Flash Card (Flash Card), at least one disk storage device, a flash memory device, or another volatile solid-state storage device. Correspondingly, the memory 910 may further include a memory controller to provide the processor 920 with access to the memory 910.

The processor 920 is a control center of the electronic device 900. The processor 902 is connected to various parts of the entire electronic device by using various interfaces and lines. The processor 902 performs various functions of the electronic device 900 and processes data by running or executing software programs and/or modules stored in the memory 910 and calling data stored in the memory 910, thereby overall monitoring the electronic device 900. The processor 920 may be a central processing unit, or may be another general-purpose processor, a digital signal processor (Digital Signal Processor, DSP), an application specific integrated circuit (Application Specific Integrated Circuit, ASIC) or a field-programmable gate array (Field-Programmable Gate Array, FPGA), or another programmable logic device, a discrete gate or a transistor logic device, a discrete hardware component, etc. The general-purpose processor may be a microprocessor, or the processor may be any conventional processor, etc.

The input unit 930 may be used to receive input numeric or character information, and generate a keyboard, a mouse, a joystick, an optical or a trackball signal input related to user settings and function control. Specifically, the input unit 930 may include a touch-sensitive surface 931 and another input device 932. Specifically, the touch-sensitive surface 931 may include but is not limited to a touch pad or a touch screen, and the another input device 932 may include but is not limited to one or more of a physical keyboard, function keys (such as volume control keys and switch keys), trackballs, a mouse, and a joystick.

The display unit 940 can be used to display information input by the user or information provided to the user as well as various graphical user interfaces of the electronic device. These graphical user interfaces can be composed of graphics, text, icons, videos, and any combination thereof. The display unit 940 may include a display panel 941. Optionally, the display panel 941 may be configured in the form of a liquid crystal display (Liquid Crystal Display, LCD), an organic light-emitting diode (Organic Light-Emitting Diode, OLED), etc.

The RF circuit 950 can be used to receive and transmit signals during the process of transmitting and receiving information or during a call. In particular, after receiving downlink information from the base station, the downlink information is handed over to one or more processors 920 for processing; in addition, uplink data is sent to the base station. Generally, the RF circuit 950 includes, but is not limited to, an antenna, at least one amplifier, a tuner, one or more oscillators, a Subscriber Identity Module (SIM) card, a transceiver, a coupler, a low noise amplifier (Low Noise Amplifier, LNA), duplexer, etc. In addition, the RF circuitry 950 can communicate with networks and other devices through wireless communication. The wireless communication can use any communication standard or protocol, including but not limited to Global System of Mobile communication (Global System of Mobile communication, GSM), General Packet Radio Service (General Packet Radio Service, GPRS), Code Division Multiple Access (Code Division Multiple Access (CDMA), Wideband Code Division Multiple Access (Wideband Code Division Multiple Access, WCDMA), Long Term Evolution (Long Term Evolution, LTE), an email, a short messaging service (Short Messaging Service, SMS), etc.

WiFi is a short-distance wireless transmission technology. The electronic device 900 can help users send and receive emails, browse web pages, access streaming media, etc. through the WiFi module 960. The WiFi module 960 provides the users with wireless broadband Internet access. Although FIG. 9 shows the WiFi module 960, it can be understood that the WiFi module 960 is not a necessary component of the electronic device 900, and can be omitted as needed without changing the essence of the invention.

The electronic device 900 further includes a power supply 970 (such as a battery) that supplies power to various components. Preferably, the power supply can be logically connected to the processor 920 through a power management system, so that functions such as charging management, discharging management, and power consumption management are implemented through the power management system. The power supply 970 may further include arbitrary components such as one or more direct current or alternating current power supplies, recharging systems, power supply failure detection circuits, power converters or inverters, and power status indicators.

It should be noted that, although not shown, the electronic device 900 may further include a Bluetooth module, etc. Details are not described herein again.

An embodiment of the present invention further provides a computer-readable storage medium, the computer-readable storage medium can be disposed in an electronic device to store at least relevant one instruction or at least one program for implementing an FFR determination method based on multi-modal medical image, and the at least one instruction or the at least one program is loaded and executed by the processor to implement the FFR determination method based on multi-modal medical image provided by the above method embodiment.

Optionally, in the embodiment of the present invention, the storage medium may include but is not limited to: a USB disk, a read-only memory (ROM, Read-Only Memory), a random access memory (RAM, Random Access Memory), a mobile hard disk, a magnetic disk, or an optical disk and other media that can store program code.

An embodiment of the present invention further provides a computer program product or a computer program. The computer program product or the computer program includes a computer instruction, and the computer instruction is stored in the computer-readable storage medium. The processor of the computer device reads the computer instruction from the computer-readable storage medium, and the processor executes the computer instruction, so that the computer device performs the FFR determination method based on multi-modal medical image provided in the above various optional implementation examples.

It should be noted that the order of the embodiments of the present invention is only for description and does not represent the advantages and disadvantages of the embodiments. Specific embodiments of the description have been described above. Other embodiments are within the scope of the appended claims. In some cases, the actions or steps described in the claims can be performed in a different order than that in the embodiments and still achieve the desired results. Additionally, the processes depicted in the drawings do not necessarily require the specific order shown or a sequential order, to achieve desirable results. In certain implementations, multitasking processing and parallel processing are also possible or may be advantageous.

Each embodiment in the description is described in a progressive manner. For the same and similar parts between the various embodiments, reference can be made to each other. Each embodiment focuses on its differences from other embodiments. In particular, for the apparatus embodiment, because the apparatus embodiment is basically similar to the method embodiment, the apparatus embodiment is described relatively simple. For relevant details, please refer to the partial description of the method embodiment.

The person of ordinary skill in the art can understand that all or part of the steps to implement the above embodiments can be completed by hardware, or can be completed by instructing relevant hardware through a program. The program can be stored in a computer-readable storage medium. The storage medium mentioned above can be a read-only memory, a magnetic disk, or an optical disk, etc.

The above embodiments are only preferred embodiments of the present invention and are not intended to limit the present invention. Any modifications, equivalent substitutions, improvements, etc. made within the spirit and principles of the present invention shall be included in the scope of protection of the present invention.

The invention claimed is:

1. An FFR determination method based on multi-modal medical image, comprising:

obtaining an intravascular image comprising a blood vessel segment of interest;

obtaining an extravascular image comprising a blood vessel segment to be detected, wherein the blood vessel segment to be detected at least partially coincides with the blood vessel segment of interest;

performing registration on the intravascular image and the extravascular image to obtain a registration result; and determining a target fractional flow reserve based on multi-modal medical image by using the registration result on the basis of the intravascular image and the extravascular image;

wherein the determining a target fractional flow reserve based on multi-modal medical image by using the registration result on the basis of the intravascular image and the extravascular image comprises:

determining a first retracement curve corresponding to a fractional flow reserve of the blood vessel segment of interest based on the intravascular image;

determining a second retracement curve corresponding to a fractional flow reserve of the blood vessel segment to be detected based on the extravascular image; and determining a target fractional flow reserve based on multi-modal medical image by using the registration result on the basis of the first retracement curve and the second retracement curve;

wherein the determining a target fractional flow reserve based on multi-modal medical image by using the registration result on the basis of the first retracement curve and the second retracement curve comprises:

determining a first fractional flow reserve sequence based on the first retracement curve, wherein the first fractional flow reserve sequence is corresponding to a first blood vessel position sequence of the blood vessel segment of interest in the intravascular image;

determining a second fractional flow reserve sequence based on the second retracement curve, wherein the second fractional flow reserve sequence is corresponding to a second blood vessel position sequence of the blood vessel segment to be detected in the extravascular image, and the second blood vessel position sequence at least partially coincides with the first blood vessel position sequence;

fusing the first fractional flow reserve sequence and the second fractional flow reserve sequence by using the registration result to obtain a target fractional flow reserve sequence; and determining a target fractional flow reserve based on multi-modal medical image on the basis of the target fractional flow reserve sequence.

2. The method according to claim 1, wherein the performing registration on the intravascular image and the extravascular image to obtain a registration result comprises:

obtaining a first feature information of the blood vessel segment of interest in the intravascular image, wherein the first feature information comprises internal lumen information of the blood vessel segment of interest;

obtaining a second feature information of the blood vessel segment to be detected in the extravascular image, wherein the second feature information comprises external lumen information of the blood vessel segment to be detected; and performing registration based on the first feature information and the second feature information to obtain a registration result.

3. The method according to claim 1, wherein the determining a first retracement curve corresponding to a fractional flow reserve of the blood vessel segment of interest based on the intravascular image comprises:

obtaining a blood flow velocity of the blood vessel segment to be detected; and determining a first retracement curve corresponding to a fractional flow reserve of the blood vessel segment of interest based on the intravascular image and the blood flow velocity.

4. The method according to claim 1, wherein the determining a first retracement curve corresponding to a fractional flow reserve of the blood vessel segment of interest based on the intravascular image comprises:

obtaining a first branch blood vessel information of the blood vessel segment of interest, wherein the first branch blood vessel information comprises branch opening information obtained based on the intravascular image, and branch information obtained based on the extravascular image; and determining a first retracement curve corresponding to a fractional flow reserve of the blood vessel segment of interest based on the intravascular image and the first branch blood vessel information.

5. The method according to claim 1, wherein the determining a second retracement curve corresponding to a fractional flow reserve of the blood vessel segment to be detected based on the extravascular image comprises:

obtaining a blood flow velocity of the blood vessel segment to be detected; and determining a second retracement curve corresponding to a fractional flow reserve of the blood vessel segment to be detected based on the extravascular image and the blood flow velocity.

6. The method according to claim 1, wherein the determining a second retracement curve corresponding to a fractional flow reserve of the blood vessel segment to be detected based on the extravascular image comprises:

obtaining a second branch blood vessel information of the blood vessel segment to be detected, wherein the second branch blood vessel information comprises branch opening information obtained based on the intravascular image, and branch information obtained based on the extravascular image; and determining a second retracement curve corresponding to a fractional flow reserve of the blood vessel segment to be detected based on the extravascular image and the second branch blood vessel information.

7. The method according to claim 1, wherein the fusing the first fractional flow reserve sequence and the second fractional flow reserve sequence by using the registration result to obtain a target fractional flow reserve sequence comprises:

calculating a first difference sequence based on the first fractional flow reserve sequence, wherein a value in the first difference sequence is a decrease value of a fractional flow reserve of a corresponding position relative to a fractional flow reserve of a previous position in the first fractional flow reserve sequence;

calculating a second difference sequence based on the second fractional flow reserve sequence, wherein a value in the second difference sequence is a decrease value of a fractional flow reserve of a corresponding position relative to a fractional flow reserve of a previous position in the second fractional flow reserve sequence;

fusing the first difference sequence and the second difference sequence by using the registration result to obtain a target difference sequence; and determining the target fractional flow reserve sequence based on the target difference sequence.

8. The method according to claim 1, wherein the determining a target fractional flow reserve based on multi-modal medical image by using the registration result on the basis of the intravascular image and the extravascular image comprises:

obtaining a first feature information of the blood vessel segment of interest in the intravascular image, wherein the first feature information comprises internal lumen information of the blood vessel segment of interest;

obtaining a second feature information of the blood vessel segment to be detected in the extravascular image, wherein the second feature information comprises external lumen information of the blood vessel segment to be detected; and calculating the target fractional flow reserve based on multi-modal medical image by using the registration result on the basis of the first feature information and the second feature information.

9. The method according to claim 1, wherein the determining a target fractional flow reserve based on multi-modal medical image by using the registration result on the basis of the intravascular image and the extravascular image comprises:

performing image fusion on the intravascular image and the extravascular image by using the registration result to obtain a fused image;

obtaining fusion feature information of the blood vessel segment to be detected in the fused image, wherein the fusion feature information comprises fusion lumen information; and calculating the target fractional flow reserve based on multi-modal medical image on the basis of the fusion feature information.

10. An electronic device, wherein the electronic device comprises a processor and a memory, at least one instruction or at least one program is stored in the memory, and the at least one instruction or the at least one program is loaded and executed by the processor to implement the FFR determination method based on multi-modal medical image according to claim 1.

11. A non-transitory computer-readable storage medium, wherein at least one instruction or at least one program is stored in the non-transitory computer-readable storage medium, and the at least one instruction or at least one program is loaded and executed by a processor to implement the FFR determination method based on multi-modal medical image according to claim 1.

12. An FFR determination apparatus based on multi-modal medical image, comprising:

an intravascular image obtaining module, configured to obtain an intravascular image comprising a blood vessel segment of interest;

an extravascular image obtaining module, configured to obtain an extravascular image comprising a blood vessel segment to be detected, wherein the blood vessel segment to be detected at least partially coincides with the blood vessel segment of interest;

a registration module, configured to perform registration on the intravascular image and the extravascular image to obtain a registration result; and a fractional flow reserve determining module, configured to determine a target fractional flow reserve based on multi-modal medical image by using the registration result on the basis of the intravascular image and the extravascular image;

wherein to determine a target fractional flow reserve based on multi-modal medical image by using the registration result on the basis of the intravascular image and the extravascular image comprises:

to determine a first retracement curve corresponding to a fractional flow reserve of the blood vessel segment of interest based on the intravascular image;

to determine a second retracement curve corresponding to a fractional flow reserve of the blood vessel segment to be detected based on the extravascular image; and to determine a target fractional flow reserve based on multi-modal medical image by using the registration result on the basis of the first retracement curve and the second retracement curve;

wherein to determine a target fractional flow reserve based on multi-modal medical image by using the registration result on the basis of the first retracement curve and the second retracement curve comprises:

to determine a first fractional flow reserve sequence based on the first retracement curve, wherein the first fractional flow reserve sequence is corresponding to a first blood vessel position sequence of the blood vessel segment of interest in the intravascular image;

to determine a second fractional flow reserve sequence based on the second retracement curve, wherein the second fractional flow reserve sequence is corresponding to a second blood vessel position sequence of the blood vessel segment to be detected in the extravascular image, and the second blood vessel position sequence at least partially coincides with the first blood vessel position sequence;

to fuse the first fractional flow reserve sequence and the second fractional flow reserve sequence by using the registration result to obtain a target fractional flow reserve sequence; and to determine a target fractional flow reserve based on multi-modal medical image on the basis of the target fractional flow reserve sequence.

* * * * *